US006783759B2

(12) United States Patent
Rosengard

(10) Patent No.: US 6,783,759 B2
(45) Date of Patent: Aug. 31, 2004

(54) COMPOSITIONS AND METHODS FOR MODULATING VARIOLA VIRUS

(75) Inventor: Ariella M. Rosengard, Gladwyne, PA (US)

(73) Assignee: Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 10/108,311

(22) Filed: Mar. 27, 2002

(65) Prior Publication Data

US 2004/0038196 A1 Feb. 26, 2004

(51) Int. Cl.[7] .......................... A61K 39/42; C12Q 1/70; C07K 16/08

(52) U.S. Cl. ............................... 424/147.1; 424/139.1; 435/5; 530/388.3

(58) Field of Search ........................... 424/147.1, 139.1, 424/159.1, 192.1, 232.1, 186.1; 435/5, 235.1; 530/388.3, 389.4, 387.9, 350; 514/12

(56) References Cited

U.S. PATENT DOCUMENTS

| 5,157,110 A | 10/1992 | Kotwal et al. ............... 530/350 |
| 5,843,778 A | 12/1998 | Rosengard et al. ......... 435/325 |

FOREIGN PATENT DOCUMENTS

| WO | WO 93/19183 | 9/1993 | |
| WO | WO 95/20660 | 8/1995 | |
| WO | WO 99/44625 | 9/1999 | |
| WO | 99/44625 | * 9/1999 | .......... A61K/38/00 |

OTHER PUBLICATIONS

Isaacs et al. Proceedings of the National Academy of Sciences USA 89:628–632, 1992.*
Lubinski et al (Seminars in cell & developmental biology, Jun. 1998, 9 (3) p329–37, abstract only cited).*
Uvarova et al. Virus Research 81:39–45, 2001.*
Henderson et al. Journal of Molecular Biology 307:323–339, 2001.*
Cooper N.R., "Complement and Viruses", The Human Complement System in Health and Disease, vol. 1, Editors Volanakis J.E. and Frank M.M. 393–407 Marcel Dekker, Inc. New York 1998.
Conry et al., "Immune Response to a Carcinoembryonic Antigen Polynucleotide Vaccine", Cancer Research 1994 54:1164–1168.
Cox et al., "Bovine Herpesvirus 1:Immune Responses in Mice and Cattle Injected with Plasmid DNA", Virology 1993 67(9): 5664–5667.
Dalmasso A.P., "Role of Complement in Graft Rejection", In:The Complement System, vol. 1 (editors Rother, K., Till, G.O., & Hänsch, G.M.) Springer–Verlag, Berlin 1997 471–486.

Davis et al., "DNA–based immunization induces continuous secretion of hepatitis B surface antigen and high levels of circulating antibody", Human Molecular Genetics 1993 2(11):1847–1851.
DePraval et al., "Variability of Interchain Binding of Immunoglobulins" Nature 1970 228:930–932.
Dempsey et al., "C3d of Complement as a Molecular Adjuvant:Bridging Innate and Acquired Immunity", Science 1996 271:348–350.
Donnelly et al., "Preclinical efficacy of a prototype DNA vaccine:Enhanced protection against antigenic drift in influenza virus", Nature Medicine 1995 1(6):583–587.
Fynan et al., "Use of DNA Encoding Influenza Hemagglutinin as an Avian Influenza Vaccine", DNA and Cell Biology 1993 12(9):785–789.
Fynan et al., "DNA vaccines: Protective immunizations by parenteral, mucosal, and gene–gun inoculations", Proc. Natl. Acad. Sci. USA 1993 90:11478–11482.
Harlow and Lane—Antibodies:A Laboratory Manual—Cold Spring Harbor Laboratory, New York 1988 Chapter 14 553–612.
Isaacs et al., "Vaccinia virus complement–control protein prevents antibody–dependent complement–enhanced neutralization of infectivity and contributes to virulence", Proc. Natl. Acad. Sci. USA 1992 89:628–632.
Kalli et al., "Mapping of the C3b–binding Site of CR1 and Construction of a $(CR1)_2$–F(ab')$_2$ Chimeric Complement Inhibitor", J. Exp. Med 1991 174:1451–1460.
Kennedy et al., "Protein–Protein Coupling Reactions and the Applications of Protein Conjugates", Clinica Chimica Acta 1976 70:1–31.
Khaw et al., "Radiochemistry and Radiopharmaceuticals—Technetium–99m Labeling of Antibodies to Cardiac Myosin Fab and to Human Fibrinogen", J. Nucl. Med. 1982 1011–1019.
Kitamura H., "Interspecies Incompatibilities of Complement Factors and Regulators", In:The Complement System, vol. 1 (editors Rother, K., Till, G.O., & Hänsch, G.M.) Springer–Verlag, Berlin 1998.
Klickstein et al., "Identification of Distinct C3b and C4b Recognition Sites in the Human C3b/C4b Receptor (CR1, CD35) by Deletion Mutagenesis", J. Exp. Med. 1988 168:1699–1711.
Köler and Milstein, "Continuous cultures of fused cells secreting antibody of predefined specificity", Nature 1975 256:495–497.
Kotwal et al., "Vaccinia virus encodes a secretory polypeptide structurally related to complement control proteins", Nature 1988 335:176–178.

(List continued on next page.)

Primary Examiner—Mary E. Mosher
(74) Attorney, Agent, or Firm—Licata & Tyrrell P.C.

(57) ABSTRACT

Antibodies directed to SPICE which may be used for detection, prevention, and treatment of variola virus are provided. Recombinant SPICE and VCP proteins are also provided which are used for enhancing the immune response to variola virus. Furthermore, modulation of complement activation by administering recombinant SPICE and VCP is provided.

6 Claims, No Drawings

OTHER PUBLICATIONS

Kotwal et al., "Inhibition of the Complement Cascade by the Major Secretory Protein of Vaccinia Virus", Science 1990 250:827–830.

Kyrch et al., "Analysis of the Functional Domains of Complement Receptor Type 1 (C3b/C4b Receptor; CD35) by Substitution Mugagenesis", J. Biol. Chem. 1994 269:13273–13278.

Kyrch et al., "Sites within the complement C3b/C4b receptor important for the specificity of ligand binding", Proc. Natl. Acad. Sci. USA 1991 88:4353–4357.

Lachmann et al., "Complement and immunity to viruses", Immunological Reviews 1997 159:69–77.

Lachmann P.J., "Microbial subversion of the immune response", PNAS 2002 99(13):8461–8462.

Liszewski et al., "Regulatory Proteins of Complement" In:The Human Complement System in Health and Disease vol. 1 Editors Volanakis J.E. & Frank M.M. Marcel Dekker, Inc. New York 1998 149–166.

Massung et al., "Terminal Region Sequence Variations in Variola Virus DNA", Virology 1996 221:291–300.

McKenzie et al., "Regulation of Complement Activity by Vaccinia Virus Complement–Control Protein", J. Infect. Dis. 1992 166:1245–1250.

Montgomery et al., "Heterologous and Homologous Protection Against Influenza A by DNA Vaccination:Optimization of DNA Vectors", DNA Cell Biol. 1993 12(9):777–783.

Moss B., "Genetically engineered poxviruses for recombinant gene expression, vaccination, and safety", Proc. Natl. Acad. Sci. USA 1996 93:11341–11348.

Mroczkowski et al., "Secretion of Thermostable DNA Polymerase Using a Novel Baculovirus Vector", J. Biol. Chem. 1994 269(18):13522–13528.

Pangburn et al., "Human Complement C3b Inactivator:Isolation, Characterization, and Demonstration of an Absolute Requirement for the Serum Protein β1H for Cleavage of C3b and C4b and Solution", J. Exp. Med. 1977 146:257–270.

Raz et al., "Intradermal gene immunization:The possible role of DNA uptake in the induction of cellular immunity to viruses", Proc. Natl. Acad. Sci. USA 1994 91:9519–9523.

Robinson et al., "Protection against a lethal influenza virus challenge by immunization with a haemagglutinin–expressing plasmid DNA", Vaccine 1993 11:957–960.

Ropp et al., "PCR Strategy for Identification and Differentiation of Smallpox and Other Orthopoxviruses", J. Clin. Microbiol. 1995 33(8):2069–2076.

Rosengard et al., "Functional characterization of soluble and membrane–bound forms of vaccinia virus complement control protein (VCP)", Mol. Immunol. 1999 36:689–697.

Rosengard et al., "Variola virus immune evasion design:Expression of a highly efficient inhibitor of human complement", PNAS 2002 99(13):8803–8813.

Ross et al., "C3d enhancement of antibodies to hemagglutinin accelerates protection against influenza virus challenge", Nat. Immunol. 2000 1(2):127–131.

Ross et al., "Generation of Three Different Fragments of Bound C3 with Purified Factor 1 or Serum", J. Immunol. 1982 129(5):2051–2060.

Sahu et al., "Interaction of Vaccinia Virus Complement Control Protein with Human Complement Proteins:Factor I–Mediated Degradation of C3b to $iC3b_1$ Inactivates the Alternative Complement Pathwayl", J. Immunol. 1998 160:5596–5604.

Schuurs et al., "Enzyme–Immunoassay", Clin. Chim. Acta 1977 81:1–40.

Shchelkunov et al., "Genes of variola and vaccinia viruses necessary to overcome the host protective mechanisms", FEBS Lett. 1993 319:80–83.

Sedegah et al., "Protection against malaria by immunization with plasmid DNA encoding circumsporozoite protein", Proc. Natl. Acad. Sci. USA 1994 91:9866–9870.

Ulmer et al., "Heterologous Protection Against Influenza by Injection of DNA Encoding a Viral Protein", Science 193 259:1745–1749.

Wang et al., "Gene inoculation generates immune responses against human immunodeficiency virus type 1", Proc. Natl. Acad. Sci. USA 1993 90:4156–4160.

Webster et al., "Protection of ferrets against influenza challenge with a DNA vaccine to the hemagglutinin", Vaccine 1994 12:1495–1498.

Wesman et al., "Soluble Human Complement Receptor Type 1:In Vivo Inhibitor of Complement Suppressing Post–Ischemic Myocardial Inflammation and Necrosis", Science 249:146–151.

Xiang et al., "Vaccination with a Plasmid Vector Carrying the Rabies Virus Glycoprotein Gene Induces Protective Immunity against rabies Virus", Virology 1994 199:132–140.

Yankauckas et al., "Long–Term Anti–Nucleoprotein Cellular and Humoral Immunity Is Induced by Intramuscular Injection of Plasmid DNA Containing NP Gene", DNA Cell Biol. 1993 12:771–776.

\* cited by examiner

COMPOSITIONS AND METHODS FOR MODULATING VARIOLA VIRUS

BACKGROUND OF THE INVENTION

Variola virus, the most virulent member of the genus Orthopoxvirus, specifically infects humans. Variola causes smallpox, which has a 30–40% mortality. Protocols for vaccination rely on the vaccinia virus which has multiple, potential side effects. The United States stopped vaccinating the public in 1972, while worldwide vaccination terminated in the late 1970s. Only 10–20% of individuals previously vaccinated are still protected due to waning immunity. Public health concerns regarding the re-emergence of variola virus has led to renewed interest in the pathogenesis of smallpox. Since ethical and public health concerns preclude in vivo work on variola virus, and the World Health Organization prohibits DNA recombination studies between variola and other Orthopoxvirus genomes, studies of variola require circuitous approaches. In vivo model systems involving orthopoxviruses do exist but are limited primarily to vaccinia, cowpox, and ectromelia viruses, which do not cause disease in immunocompetent humans (Moss (1996) Proc. Natl. Acad. Sci. USA 93:11341-11348). Therefore, the relative benignity of other orthopoxviruses in humans may underestimate the importance of any homologous protein in the pathogenesis of smallpox.

Protocols for resuming the administration of smallpox virus also have serious implications. In the last decades, the growing number of immunocompromised patients suffering from AIDS, diabetes, cancer and other conditions has increased. In addition, the widespread use of immunosuppressants for organ transplant patients, the common practice of radiation and chemotherapy for treating malignancies, as well as the growing size of the aging population have also increased. Administration of the current smallpox vaccine and subsequent shedding of this virus may result in widespread vaccinia virus infection in the population of immunocompromised individuals. Therefore, alternative smallpox vaccines are imperative at this time.

Complement regulatory proteins (CRPs), encoded by genes located in the terminal regions of orthopoxviruses, are important for viruses to evade a host-mediated complement attack (Cooper, N. R. Complement and Viruses. In: The Human complement System in Health and Disease, Vol. 1 (eds. Volanakis, J. E. & Frank, M. M.) 393–407, Marcel Dekker, Inc. NY, 1998). Virally-encoded CRPs presumably deflect complement destruction of infected host cells to allow for more efficient viral spread (Shchelkunov et al. (1993) FEBS Lett. 319:80–83; Lachmann and Davies (1997) Immunological Reviews 159:69–77). CRPs differ with respect to ligand specificity (C3b and/or C4b) and the mechanism of convertase inactivation. They may accelerate the normal decay of the classical and alternative pathway convertases or function as cofactors for the serine protease, factor I, to enzymatically cleave the α' chains of C3b and C4b into smaller, inactive fragments (Liszewski and Atkinson. Regulatory Proteins of Complement. In: The Human complement System in Health and Disease, Vol. 1 (eds. Volanakis, J. E. & Frank, M. M.) 149–166, Marcel Dekker, Inc. NY, 1998). Structurally, CRPs are composed of 4–56 homologous motifs, termed short consensus repeats (SCR).

Vaccinia Virus Complement Control Protein (VCP) is a CRP produced by vaccinia virus that has been shown to enhance the virulence of vaccinia in rabbit and guinea pig experimental models and causes larger lesions when injected intradermally (Isaacs et al. (1992) Proc. Natl. Acad. Sci. USA 89:628–632). VCP functions primarily as a cofactor for factor I rather than as a decay accelerator (Kotwal et al. (1990) Science 250:827–830; McKenzie et al. (1992) J. Infect. Dis. 166:1245–1250; Sahu et al. (1998) J. Immunol. 160:5596–5604). Hence, Kotwal et al. (U.S. Pat. No. 5,157,110) describe the use of VCP to bind to C4b and inhibit the complement cascade. Furthermore, Rosengard et al. (U.S. Pat. No. 5,843,778) disclose the use of recombinant, VCP-immunoglobulin Fc region fusion protein to modulate complement activation through binding of complement components C3b and C4b.

DNA comparison studies revealed that the genomes of all variola virus strains also encode a CRP homolog consisting of 4 SCRs (Massung et al. (1996) Virology 221:291–300). This Smallpox Inhibitor of Complement Enzyme (SPICE) differs from the VCP amino acid sequence by 4.6%; the 11 amino acid differences are dispersed throughout SCR2, 3, and 4. In the absence of wild-type variola proteins, Rosengard et al. (PCT Publication WO 99/44625) describes a SPICE polypeptide that has been generated by molecular engineering of VCP. The intended use of this SPICE protein, fused to an immunoglobulin molecule, is to modulate complement activation.

To date, there are few options for the rapid detection of smallpox infection. Ropp et al. ((1995) J. Clin. Microbiol. 33:2069–76) demonstrate the use of a combined PCR amplification-endonuclease digestion of the hemagglutinin gene to identify and differentiate smallpox from other orthopoxviruses. Moreover, Hooper et al. (U.S. patent application Ser. No. 20020009447, filed Jan. 24, 2002) describe the use of monoclonal antibodies directed to vaccinia L1R and A33R antigens to detect, prevent, and/or treat vaccinia virus infections in vitro and in vivo. Monoclonal antibodies directed to orthopoxvirus homologs of vaccinia L1R and A33R are also disclosed.

The present invention addresses the needs of improved detection, prevention, and treatment of variola virus infection. Antibodies directed against SPICE protein and SPICE-specific primers for PCR amplification of the SPICE gene are provided for the detection of variola virus. The present invention also addresses the need for improved vaccines for the prevention of variola virus infection by providing antibodies directed against SPICE for passive vaccination. Furthermore, the present invention provides SPICE fusion proteins for vaccination against smallpox virus. Treatment for variola virus infections is provided through administration of an antibody directed against SPICE. Finally, SPICE fusion proteins are described for binding human complement components to modulate complement activation.

SUMMARY OF THE INVENTION

The present invention provides antibodies against Smallpox Inhibitor of Complement Enzyme (SPICE).

An object of the present invention is to provide a method of preventing or treating variola virus infection by administering anti-SPICE antibodies.

Another object of the present invention is to provide a method of co-administering anti-VCP/SPICE antibodies with vaccinia virus vaccine to modulate vaccine side effects.

Another object of the present invention is to provide a method for detecting variola virus infections in humans by detecting the presence of SPICE protein or nucleic acid sequences encoding SPICE.

A further object of the present invention provides kits for the detection of SPICE or nucleic acid sequences encoding SPICE.

Another object of the present invention is to provide a vaccine for variola virus by administering recombinant SPICE and VCP proteins to enhance the immune response to variola virus or administering a SPICE or VCP DNA vaccine.

A further object of the present invention is directed to the modulation of complement activation by administering recombinant SPICE and VCP proteins.

The foregoing and other objects and aspects of the present invention are explained in detail in the specification set forth below.

DETAILED DESCRIPTION OF PREFERRED EMBODIMENTS

While the virulence of orthopoxviruses naturally represents the cumulative effects of all of their proteins, SPICE appears to function as a potent inhibitor of human complement thereby creating a microenvironment around variola-infected cells so as to protect them from complement-mediated attack while they serve as a site for viral replication. To facilitate the study of SPICE's function, monoclonal antibodies were raised against VCP to detect SPICE. Though monoclonal antibodies were used in the present invention, molecules or active fragments of molecules that bind to known antigens are also to be considered. Examples of active fragments of molecules that bind to known antigens include Fab and $F(ab')_2$ fragments. These active fragments may be derived from an antibody of the present invention by a number of techniques. For example, purified monoclonal antibodies may be cleaved with an enzyme, such as pepsin, and subjected to HPLC gel filtration. The appropriate fraction containing Fab fragments may then be collected and concentrated by membrane filtration and the like. For further description of general techniques for the isolation of active fragments of antibodies, see for example, Khaw, et al. ((1982) *J. Nucl. Med.* 23:1011–1019). The term "antibody" also includes bispecific and chimeric antibodies.

Antibodies of the present invention were generated using classical cloning and cell fusion techniques. The antigen of interest, is typically administered (e.g., intraperitoneal injection) to wild-type or inbred mice (e.g., BALB/c) or transgenic mice which produce desired antibodies, or rats, rabbits or other animal species which may produce native or human antibodies. The antigen may be administered alone, or mixed with adjuvant, or expressed from a vector (VEE replicon vector), or as DNA, or as a fusion protein to induce an immune response. Fusion proteins comprise the peptide against which an immune response is desired coupled to carrier proteins, such as histidine tag (his), mouse IgG2a Fc domain, β-galactosidase, glutathione S-transferase, keyhole limpet hemocyanin (KLH), and bovine serum albumin, to name a few. In these cases, the peptides serve as haptens with the carrier proteins. After the animal is boosted, for example, two or more times, the spleen is removed and splenocytes are extracted and fused with myeloma cells using the well-known processes of Kohler and Milstein ((1975) *Nature* 256:495–497) and Harlow and Lane (Antibodies: A Laboratory Manual (Cold Spring Harbor Laboratory, New York (1988)). The resulting hybrid cells are then cloned in the conventional manner, e.g. using limiting dilution, and the resulting clones, which produce the desired monoclonal antibodies, are cultured.

Antibodies binding VCP/SPICE antigen are part of the present invention. These monoclonal antibodies were raised against vaccinia VPC proteins. Other orthopoxviruses are expected to contain VCP sequences at least 90% identical and which will likely produce antigens capable of eliciting protective/neutralizing antibodies. An exemplary example of a homolog of VCP is SPICE. Other homologs of SPICE or VCP having at least 90% identity exist in other orthopoxviruses are chosen from the group consisting of: buffalopox virus, syn. vaccinia subspecies (buffalo, cattle, human); camelpox virus (camel); cowpox virus (rodents, felines, bovines, human); ectromelia virus (mousepox); monkeypox virus (rodents, primates, human); rabbitpox virus, syn. vaccinia subspecies (colonized rabbit); raccoonpox virus (North America raccoon); taterapox virus (African gerbil); and volepox virus (California pinon mouse and voles). Monoclonal antibodies against homologs from these orthopoxviruses would likely be protective against challenge with the source of immunogen virus.

Once the antibodies were generated, the binding site on VCP of each antibody was determined by flow cytometry using mouse fibroblast lines expressing 2, 3 or 4 contiguous VCP short consensus repeats (SCRs) as cell surface receptors. By determining to which cell lines a mAb bound and to which cell line it did not bind, the SCR binding site of the mAb was determined. For example, mAb 5A10 recognized the three cell lines expressing SCR1 of VCP, but did not recognize the three cell lines that expressed a VCP mutant lacking SCR1. Therefore, it was concluded that mAb 5A10 recognized an epitope on SCR1. The term epitope as used herein, is generally understood by those of skill in the art to refer to the region of an antigen, such as SCR1 for example, that interacts with an antibody. An epitope of a peptide or protein antigen may be formed by contiguous or noncontiguous amino acid sequences of the antigen. VCP and SPICE, like many proteins, contains many epitopes. The epitopes or peptides recognized by the antibodies of the present invention and conservative substitutions of these peptides which are still recognized by the antibody are an embodiment of the present invention. These peptides offer a convenient method for eluting the variola or vaccinia antigen bound to the respective antibody on immunoaffinity columns. For example, when an antibody which recognizes the epitope for SPICE is used in an immunoaffinity column to purify SPICE, the peptide recognized by the antibody may be added to the immunoaffinity column to elute the SPICE. Further truncation of these epitopes may be possible since antigenic epitopes have been reported to be represented by as few as five amino acid residues. In a preferred embodiment of the present invention, monoclonal antibodies binding to SCR1 of a viral complement control protein comprise 5A10 or 6E5. In another preferred embodiment, monoclonal antibodies binding to SCR2 of a viral complement control protein comprise 3D9 or 6C4. In yet another preferred embodiment, monoclonal antibodies binding to SCR3 of a viral complement control protein comprise 2F10 or 5E7. In yet another preferred embodiment, monoclonal antibodies binding to SCR4 of a viral complement control protein comprise 1G1, 5A1 or 5E1.

The antibodies described in the present invention were determined to bind VCP and SPICE as measured in an ELISA assay and by western blot analyses. Other immunoassays that may be used to detect binding of the antibodies to an appropriate antigen include radioimmunoassay, immunofluorescent assay, chemiluminescent assay, immunohistochemical assay and the like and may be performed in vitro, in vivo or in situ. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A.

Benjamin, Inc., 1964; and Oellerich, M. (1984) *J. Clin. Chem. Clin. Biochem.* 22:895–904. Only 3 mAbs recognized recombinant SPICE (rSPICE, SPICEFc or SPICEhis) over rVCP in competitive ELISAs (Djavadi-Ohaniance and Friguet (1991) The specificity of monoclonal antibodies for enzymes in solution versus immobilized on solid phases (In: Immunochemistry of solid-phase immunoassay. J. Butler (ed.) CRC Press, Inc., Boca Raton, Fla., pp 203). In a preferred embodiment of the present invention, monoclonal antibodies binding to SPICE comprise 5A10, 5E7, or 1G1.

By further mapping of the binding site of the monoclonal antibodies described, other peptides useful as a vaccine or a therapeutic may be identified. Therefore, in another aspect, this invention relates to a method for identifying protective antigenic epitopes comprising (i) reacting a monoclonal antibody to different overlapping fragments encompassing the complete antigen, (ii) identifying a fragment to which the protective antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides may then be assayed for their ability to protect an animal from disease, or to reduce the severity of disease.

The epitopes or peptides on the SPICE antigen to which the antibodies bind may constitute all or part of an active vaccine candidate. An active vaccine or therapeutic candidate may comprise these peptide sequences and others. These may be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin may be added to increase antigen processing for more effective immune responses. In a preferred embodiment, SPICE or epitopes or peptides of the SPICE or VCP are fused to three tandem copies of C3d as described by Dempsey, et al. ((1996) *Science* 271:348–50).

This fusion protein results in 100- and 10,000-fold more immunogenic peptide by binding to complement receptor 2 (CR2;CD21).

An active vaccine or therapeutic candidate may also be in the form of a DNA vaccine. An alternative to a traditional vaccine comprising an antigen and an adjuvant, is directed to in vivo introduction of DNA encoding the antigen into tissues of a subject for expression of the antigen by the cells of the subject's tissue. Such vaccines are termed herein "DNA vaccines" or "nucleic acid-based vaccines." DNA vaccines are described in International Patent Publication WO 95/20660 and International Patent Publication WO 93/19183, the disclosures of which are hereby incorporated by reference in their entireties. The ability of directly injected DNA that encodes a viral protein to elicit a protective immune response has been demonstrated in numerous experimental systems (Conry, et al. (1994) *Cancer Res.* 54:1164–1168; Cox, et al. (1993) *Virology* 67:5664–5667; Davis, et al. (1993) *Hum. Mole. Genet.* 2:1847–1851; Sedegah, et al. (1994) *Proc. Natl. Acad. Sci. USA* 91:9866–9870; Montgomery, et al., (1993) *DNA Cell Bio.* 12:777–783; Ulmer, et al., (1993) *Science* 259:1745–1749; Wang, et al. (1993) *Proc. Natl. Acad. Sci. USA* 90:4156–4160; Xiang, et al. (1994) *Virology* 199:132–140). Studies to assess this strategy in neutralization of influenza virus have used both envelope and internal viral proteins to induce the production of antibodies, but in particular have focused on the viral hemagglutinin protein (HA) (Fynan, et al. (1993) *DNA Cell. Biol.* 12:785–789; Fynan, et al. (1993) *Proc. Natl. Acad. Sci. USA* 90:11478–11482; Robinson, et al. (1993) *Vaccine* 11:957; Webster, et al. (1994) *Vaccine* 12:1495–1498). A DNA vaccine encoding a C3d fusion of HA from influenza virus, has recently been developed (Ross, et al. (2000) *Nat. Immunol.* 1(2):127–31). Analysis of the titers, avidity maturation, and hemagglutinin-inhibition activity of raised antibody revealed that immunizations with the HA-3C3d DNA accelerated both the avidity maturation of antibody to HA and the appearance of hemagglutinin-inhibition activity. These accelerated antibody responses correlated to a more rapid appearance of protective immunity. They also correlated to complete protection from live virus challenge by a single vaccination at a dose ten times lower than the protective dose for non-C3d forms of HA.

Vaccination through directly introducing DNA that encodes a SPICE or VCP protein to elicit a protective immune response produces both cell-mediated and humoral responses. This is analogous to results obtained with live viruses (Raz, et al. (1994) *Proc. Natl. Acad. Sci. USA* 91:9519–9523; Ulmer (1993) supra; Wang (1993) supra; Xiang (1994) supra). Studies with ferrets indicate that DNA vaccines against conserved internal viral proteins of influenza, together with surface glycoproteins, are more effective against antigenic variants of influenza virus than are either inactivated or subvirion vaccines (Donnelly, et al. (1995) *Nat. Medicine* 6:583–587). Indeed, reproducible immune responses to DNA encoding nucleoprotein that last essentially for the lifetime of the animal have been reported in mice (Yankauckas, et al. (1993) *DNA Cell Biol.* 12:771–776). Accordingly, a preferred embodiment of the present invention provides a vaccine comprising DNA encoding SPICE. In a more preferred embodiment, a DNA vaccine comprises DNA encoding SPICE fused to three tandem copies of C3d.

The present invention still further pertains to a method for detecting variola in a sample suspected of containing variola. The method includes contacting the sample with an antibody which binds an epitope of SPICE antigen, allowing the antibody to bind to the SPICE antigen to form an antibody-antigen complex, washing the sample, detecting the formation of the antibody-antigen complex and correlating the presence or absence of the antibody-antigen complex with the presence or absence of SPICE antigen in the sample. The sample may be biological, environmental or a food sample.

The detection of the formation of the antibody-antigen complex is intended to include detection of the presence or absence of SPICE antigen in a sample. The presence or absence of SPICE antigen may be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York (1988) 555–612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a variola virus vaccinee and an antibody of the present invention, are allowed to compete for binding of the antigen. The amount of antibody bound is then measured, and a determination is made as to whether the serum contains SPICE antibodies. This competitive ELISA may be used to indicate immunity to known protective epitopes following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that may bind to the antigen.

These immunoassays typically rely on labeled antigens, antibodies, or secondary reagents for detection. These proteins may be labeled with radioactive compounds, enzymes, biotin, or fluorochromes. Of these, radioactive labeling may be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and may be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art know other suitable labels which may be employed in accordance with the present invention. The binding of these labels to antibodies or fragments thereof may be accomplished using standard techniques commonly known to those of ordinary skill in the art. Typical techniques are described by Kennedy, et al. ((1976) *Clin. Chim. Acta* 70:1–31), and Schurs, et al. ((1977) *Clin. Chim Acta* 81:1–40). Coupling techniques mentioned in the latter are the glutaraldehyde method, the periodate method, the dimaleimide method, and others.

The term "sample" is intended to include biological material, e.g. cells, tissues, or biological fluid as well as environmental materials, e.g., soil and water, and food samples including canned goods, meats, and others.

Yet another aspect of the present invention is a kit for detecting variola virus in a biological sample. The kit includes a container holding one or more antibodies which binds an epitope of SPICE antigen and instructions for using the antibody for the purpose of binding to SPICE antigen to form an antibody-antigen complex and detecting the formation of the antibody-antigen complex such that the presence or absence of the antibody-antigen complex correlates with presence or absence of variola virus in the sample. Examples of containers include multiwell plates which allow simultaneous detection of variola virus in multiple samples.

As described in greater detail in the examples, antibodies which bind to at least two different viral antigens, VCP and SPICE have been isolated. Hence, the reactivity of the mAbs is applicable against a broad variety of different wild type and laboratory variola and vaccinia strains of different types.

Given these results, antibodies according to the present invention are suitable both as therapeutic and prophylactic agents for treating or preventing vaccinia or variola infections. In general, this comprises administering an effective amount of one or more antibodies of the present invention to a susceptible subject or one exhibiting variola or vaccinia infection. Any active form of the antibody may be administered, including Fab and F(ab')$_2$ fragments. Antibodies of the present invention may be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the antibodies does not result in clearance of the antibodies before virus may be controlled, and the induced immune response to the antibodies in the subject does not induce "serum sickness" in the subject. Preferably, the antibodies administered exhibit some secondary functions such as binding to Fc receptors of the subject.

Treatment of individuals having variola or vaccinia infection may comprise the administration of a therapeutically effective amount of SPICE/VCP antibodies of the present invention. The antibodies may be provided in a kit as described below. The antibodies may be used or administered as a mixture, for example in equal amounts, or individually, provided in sequence, or administered all at once. In providing a patient with antibodies, or fragments thereof, capable of binding to SPICE antigen, or an antibody capable of protecting against variola virus in a recipient patient, the dosage of administered agent will vary depending upon such factors as the patient's age, weight, height, sex, general medical condition, previous medical history, etc.

In a similar approach, another therapeutic use of the antibodies of the present invention is the active immunization of a patient using an anti-idiotypic antibody raised against one of the present monoclonal antibodies. Immunization with an anti-idiotype which mimics the structure of the epitope could elicit an active anti-SPICE response (Linthicum, D. S. and Farid, N. R., Anti-Idiotypes, Receptors, and Molecular Mimicry (1988), pp 1–5 and 285–300).

Likewise, active immunization may be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host may be actively immunized with the antigenic/immunogenic peptide in pure form, a fragment of the peptide, or a modified form of the peptide. One or more amino acids, not corresponding to the original protein sequence may be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against variola virus are intended to be provided to recipient subjects in an amount sufficient to effect a reduction in the variola virus infection symptoms. An amount is said to be sufficient to "effect" the reduction of infection symptoms if the dosage, route of administration, etc. of the agent are sufficient to influence such a response. Responses to antibody administration may be measured by analysis of subject's vital signs.

A composition is said to be "pharmaceutically acceptable" if its administration may be tolerated by a recipient patient.

Such an agent is said to be administered in a "therapeutically effective amount" if the amount administered is physiologically significant. An agent is physiologically significant if its presence results in a detectable change in the physiology of a recipient patient.

The present invention still further pertains to a method of administering a therapeutically effective amount of antibodies against SPICE or VCP in conjunction with vaccinia virus vaccine to modulate side effects associated with said vaccine. Side effects associated with vaccinia virus vaccine include tissue destruction, relentless progressive pock lesions, and metastatic viral lesions at the site of inoculation. Healthy vaccines have developed accidental vaccinia infection by autoinoculation to other body sites, such as the eye; ocular vaccinia may lead to blindness. Immunosuppressed vaccines, which include pregnant women and individuals with eczema, cancer, or other immunodeficiencies, often have more severe side effects. These severe side effects include fetal vaccinia, eczema vaccinatum, vaccinia necrosum, progressive vaccinia or vaccinia gangrenosum. In a preferred embodiment, administration of SPICE or VCP antibodies capable of protecting against vaccinia virus side effects are intended to be provided to recipient subjects in an amount sufficient to effect a reduction in the vaccinia virus vaccine symptoms.

Another aspect of the present invention pertains to the administration of VCP or SPICE or derivatives thereof or DNA vaccines comprised of DNA encoding SPICE or VCP or derivatives thereof prior to the administration of vaccinia virus vaccine to attenuate the virulence of the vaccinia virus. The preimmunization step would be beneficial to immunocompromised individuals or individuals who may suffer from the side effects associated with the vaccinia virus vaccine.

The compounds of the present invention may be formulated according to known methods to prepare pharmaceutically useful compositions, whereby these materials, or their functional derivatives, are combined in admixture with an acceptable carrier. Suitable carriers and their formulation, inclusive of other human proteins, e.g., human serum albumin, are described, for example, in Remington's Pharmaceutical Sciences (16th ed., Osol, A. ed., Mack Easton Pa. (1980)). In order to form an acceptable composition suitable for effective administration, such compositions may contain an effective amount of the above-described compounds together with a suitable amount of carrier.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethyl-cellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules, for example, hydroxymethylcellulose, gelatin-microcapsules, or poly(methylmethacylate)-microcapsules, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980). Furthermore, additional pharmaceutical methods may be employed to incorporate the compositions of the present invention into as a lining of surgical tubing.

Administration of the antibodies disclosed herein may be carried out by any suitable means, including parenteral injection (such as intraperitoneal, subcutaneous, or intramuscular injection), orally, or by topical application of the antibodies (typically carried in a pharmaceutical formulation) to an airway surface. Topical application of the antibodies to an airway surface may be carried out by intranasal administration (e.g., by use of dropper, swab, or inhaler which deposits a pharmaceutical formulation intranasally). Topical application of the antibodies to an airway surface may also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique may be employed. Oral administration may be in the form of an ingestible liquid or solid formulation.

The treatment may be given in a single dose schedule, or preferably a multiple dose schedule in which a primary course of treatment may be with 1–10 separate doses, followed by other doses given at subsequent time intervals required to maintain and or reinforce the response, for example, at 1–4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Another aspect of the present invention relates to detection of nucleic acid sequences encoding SPICE. RFLP variations are present within VCP and SPICE genes digested with the restriction endonuclease SspI. This recognition site is present only in the SPICE genes of the five different variola strains sequenced to date (Variola virus strains Garcia—1966, Congo—1965, and Somalia—1977, and Variola Major virus strains India—1967 and Bangladesh—1975) due to the leucine to serine difference in SCR4 of variola versus vaccinia virus. However, the recognition site is absent in the VCP gene of two strains of vaccinia virus (Vaccinia virus strains WR and Copenhagen) and also absent in the complement regulatory protein (also known as IMP (Inflammatory Modulating Protein)), of cowpox virus strain Grishak. The present invention uses this unique restriction site in the SCR4 region of SPICE to specifically detect the presence of variola virus in a sample.

Therefore, another embodiment of the present invention relates to a method of detecting, in a sample, nucleic acid sequences encoding SPICE, involving subjecting the nucleic acid sequences to a Polymerase Chain Reaction (PCR), wherein the PCR employs at least two oligonucleotide primers that anneal to the nucleic acid sequences encoding SPICE. One of the primers is complementary to a first nucleotide sequence 5' of a diagnostic SspI site unique to the SCR4 region of variola virus SPICE. Such a primer is preferably 50, 100, or 200 bp 5' of the SSpI site and most preferably corresponds to SEQ ID NO:11. The second primer is complementary to a second nucleotide sequence 3' of a diagnostic SspI site unique to the SCR4 region of variola virus SPICE. Such a primer is preferably 50, 100, or 200 bp 3' of the SspI site and most preferably corresponds to SEQ ID NO:12. In accordance with this method, a geometrically amplified product is obtained only when the first and second nucleotide sequences occur within the same nucleic acid molecule encoding SPICE. The fundamentals of PCR are well-known to the skilled artisan, see, e.g. McPherson, et al., PCR, A Practical Approach, IRL Press, Oxford, Eng. (1991), hereby incorporated by reference. A subsequent step for the specific detection of SPICE DNA is to endonuclease digest the resulting PCR amplicon with SspI. Digestion of amplified fragments with SspI results in two fragments for the SPICE gene (approximately 576 and 157 bp) and only one fragment for the VCP or IMP gene (approximately 730 bp).

The present invention also provides kits which are useful for carrying out the present invention. The present kit comprises a container containing the above-described primers. The kit also comprises other solutions necessary or convenient for carrying out the invention. The container may be made of glass, plastic or foil and may be a vial, bottle, pouch, tube, bag, etc. The kit may also contain written information, such as procedures for carrying out the present invention or analytical information, such as the amount of reagent contained in the first container. The container may be in another container, e.g., a box or a bag, along with the written information.

A further aspect of the present invention involves fusion proteins of SPICE and VCP. Recombinant protein "rSPICE", as used herein includes, but is not limited to, histidine-tagged SPICE (SPICEhis) or mouse IgG2a Fc-tagged SPICE (SPICEFc). Likewise recombinant protein "rVCP", as used herein includes, but is not limited to, histidine-tagged VCP (VCPhis) or mouse IgG2a Fc-tagged VCP (VCPFc).

SPICE was generated by mutating VCP amino acid sequence into that of SPICE. To facilitate purification of SPICE and VCP polypeptide, his and Fc tags were fused to the polypeptides. Analysis of the fusion polypeptides revealed that SPICEhis, VCPhis, SPICEFc, and VCPFc migrated as single bands under reducing conditions on 12% sodium dodecyl sulfate-polyacrylamide gel electrophoresis (SDS-PAGE) at 33, 35, 53, and 55 kDa, respectively. The Fc-fusion polypeptides migrated at approximately 110 kDa under non-reducing conditions, representing dimers of VCP or SPICE due to disulfide bonds between two Fc domains (De Preval et al. (1970) Nature 228:930–932). The recombinant proteins produced in mammalian and insect cells migrated on SDS-PAGE and functioned identically.

The molecular mass of SPICEhis and VCPhis by mass spectrometry was 28,943 and 29,057 Da, respectively; very close to the predicted molecular masses of 28,936 and 28,818 Da, but different from the molecular mass observed on SDS-PAGE. To investigate the discrepancy between the molecular mass established by mass spectrometry versus SDS-PAGE, wild-type VCP, secreted into the media of vaccinia-infected cells, was identified by western blot and shown to co-migrate with VCPhis at approximately 35 kDa, consistent with previously published mass of wild-type VCP (Kotwal, et al. (1990) Science 250:827–830). Moreover, glycosylation experiments were negative and mass spectrometry analysis detected no evidence of glycosylation or acylation. Therefore, the discrepancy in the apparent molecular mass of viral complement regulatory proteins (CRPs) on SDS-PAGE with the determined value by mass spectrometry may be artifactual.

The molecular engineering and expression of SPICE confirmed that variola produces a compact, functionally active cofactor for factor I. C3b degradation experiments were performed to compare the cofactor activity of SPICE, VCP, soluble human CR1 (sCR1; Weisman, et al. (1990) Science 249:146–151), and H factor at normal ionic strength. Soluble CR1 is a recombinant, soluble protein consisting of 30 SCRs of CR1, but lacking the transmembrane and cytoplasmic domains (Weisman, et al. (1990) Science 249:146–151). Soluble CR1 is the most potent inhibitor of complement activation known, however, it is eight times larger in size than SPICE. The C3bα' cleavage fragments migrate as follows: 68 kDa, 46 kDa (iC3b$_1$), 43 kDa (iC3b$_2$), and <35 kDa (C3dg/C3c). C4bα' cleavage fragments migrate as follows: 64 kDa (iC4b), 46 kDa (C4d), and 25 kDa (C4c).

The cofactor activity of SPICE was robust, with C3b cleavage to iC3b$_2$ occurring almost immediately, followed by cleavage to C3c/C3dg (sampled at 4 and 24 hours). In the presence of VCP, C3b was degraded more slowly, first to iC3b$_1$ and then to iC3b$_2$. However, VCP did not participate in further degradation of iC3b$_2$ to C3c/C3dg, even after 24 hours. Therefore, qualitatively, SPICE functions more like factor H, which serves as a cofactor for factor I in the degradation of iC3b$_2$ to C3c/C3dg after longer incubations (Ross, et al. (1982) J. Immunol. 129:2051–2060). Although not as potent as sCR1, SPICE may result in a similar degradation pattern where C3dg is formed (Weisman, et al. (1990) Science 249:146–151). Identical experiments were performed for C4b. At this concentration of SPICEhis and VCPhis (0.65 pM), the cofactors appear to function identically and result in the degradation of C4b to C4c/C4d. Factor H also works as a cofactor for factor I degradation of C4b in the fluid phase (Pangburn, et al. (1977) J. Exp. Med. 146:257–270).

Using 100-fold lower concentrations (0.68 pM) of recombinant cofactors than that used in the previous experiment, differences in efficiency could be established. In the presence of SPICEhis, 50% of the C3α' chain was degraded in less than 5 minutes, and entirely degraded by 15 minutes, as compared to nearly complete degradation of the C3α' chain in 7 minutes by sCR1. However, only 25% of the C3bα' chain was degraded after 120 minutes with VCP. Therefore, SPICEhis functions as a cofactor for factor I in the degradation of C3b with at least 100-fold greater efficiency than VCPhis. Soluble CR1 functions at least twice as fast as SPICEhis possibly due to the three ligand binding sites of CR1 (Klickstein, et al. (1988) J. Exp. Med. 168:1699–711; Krych, et al. (1991) Proc. Natl. Acad. Sci. USA 88:4353–7; Kalli, et al. (1991) J. Exp. Med. 174:1451–60; Krych, et al. (1994) J. Biol. Chem. 269:13273–8). Furthermore, at this low concentration of SPICE and VCP, the degradation patterns showed that with SPICEhis, the C3bα' chain was immediately cleaved to iC3b$_1$, followed by cleavage to iC3b$_2$, while with VCPhis, no such degradation to iC3b$_2$ was observed, consistent with Sahu, et al. ((1998) J. Immunol. 160:5596–5604). Unlike cobra venom factor and Compstatin, a 13-residue cyclic peptide complement inhibitor, which inhibit cleavage of C3, SPICE inhibits the active form of C3, i.e., C3b.

Similarly, kinetic experiments using C4b were performed. At limiting concentration of recombinant proteins (0.68 pM), 50% of the C4bα' chain was degraded in 15 minutes with sCR1, 20 minutes with SPICEhis, and 120 minutes with VCPhis. At this concentration, therefore, SPICEhis functions approximately 6-fold faster than VCPhis, but slower than sCR1. Minimal improvement in SPICEhis and VCPhis cofactor activity with both ligands (C3b and C4b) was observed at half-ionic strength solution. Accordingly, a preferred embodiment of the present invention provides a fusion protein comprising SPICE and a tag comprising his or Fc that binds human complement components C4b, C3b, iC3b$_1$, iC3b$_2$, iC4b, or C4c. In a preferred embodiment, the SPICE fusion protein binds complement components C3b or C4b.

Monoclonal antibodies binding to SPICE or VCP were tested for their use in inhibiting SPICE or VCP in the degradation of C3b or C4b. Results indicated that both 1G1 and 5E7 inhibited the degradation of C3b and C4b by SPICE, while mAbs 6E5 (anti-SCR1), 3D9 (anti-SCR2), 6C4 (anti-SCR2), and 1G1 inhibited the function of VCP in the degradation of both ligands. In addition, 5E1 (anti-SCR4) inhibited VCP in the degradation of C3b only. These data suggest that SCR4 is critical for VCP and SPICE cofactor activity, while SCR2 is also critical for VCP. Due to the large size of immunoglobulin, however, the possibility of blocking as a result of stearic hindrance effects should also be considered.

Since mammalian CRPs exhibit homologous restriction, that is, they function best against complement from phylogenetically related species (Dalmasso, A. P. Role of Complement in Graft Rejection. In *The Complement System*, Vol. 1 (eds. Rother, K., Till, G. O., & Hansch, G. M.) 471–486 (Springer-Verlag, Berlin, 1997)), it was determined whether variola exhibits "host complement restriction", particularly due to its restricted host range. Therefore, the ability of rSPICE and rVCP to inhibit complement from human, baboon, dog, guinea pig was tested in hemolytic assays.

From these experiments it was shown that both complement pathways were inhibited by rSPICE and rVCP. However, relative to VCPFc, SPICEFc preferentially inhibited human and baboon complement versus dog and guinea pig complement. Similarly, relative to VCPhis, SPICEhis preferentially inhibited human and baboon complement versus dog and guinea pig complement. In these experiments, however, Fc constructs behaved less efficiently than the his-tagged constructs possibly as a result of the Fc constructs forming dimers between the Fc domains; the cofactor's function may be more potent in the monomeric, his-tagged form. Since the specific interaction between cofactor proteins, ligands, and factor I have not been clearly defined, it is not clear the role that a dimeric form might have on the interaction of these components. Fc fusions are preferred because they last longer in the blood, therefore, Fc constructs may be modified to block disulfide bond formation which lead to Fc dimers. Nonetheless, the hemolysis studies suggest that the complement preference of SPICE parallels the host preference of the virus. Accordingly, a preferred embodiment of the present invention is a fusion protein comprising a tag fused to SPICE.

In a further aspect, the invention provides a method for modulating a complement-mediated disorder in a mammal, i.e., any condition in which complement activity is undesirably high. Examples of complement-mediated disorders include, but are not limited to, inflammation (including neurological inflammation), spinal cord injuries, arthritis, ischemia-induced reperfusion injuries, glomerulonephritis, encephalomyelitis, and burns. Also, to be considered are situations where complement activation leads to increased morbidity, such as occurs when serum, plasma or blood is perfused through tubing or plastics as in cardiopulmonary bypass, dialysis and the like. An inhibition effective amount of rSPICE or rVCP is an amount that inhibits at least 20%, preferably 50%, and most preferably 90% of complement activity. If desired, an inhibition effective amount of rSPICE or rVCP may be identified as an amount that ameliorates a sign(s) or symptom(s) of a complement-mediated disorder. The examples, which follow, are set forth to illustrate the present invention, and are not to be construed as limiting thereof.

EXAMPLE 1

Molecular Engineering, Expression and Purification of Recombinant SPICE

SPICE was generated by mutating the VCP amino acid sequence into that of SPICE. Thirteen nucleotide mutations, generated using standard methods, resulted in 11 amino acid substitutions (Table 1). Twenty-two primers (Life Technologies, Inc, (LTI) Grand Island, N.Y.) were designed with the following point mutations: T was substituted for A at position 339 of the VCP DNA sequence (Kotwal and Moss (1988) *Nature* 335:176–178), T for C400, A for C416, A for G430, A for G466, T for C500, AAT for GAG 538–540, A for G640, T for C686, C for A749, and C for A814. The DNA sequence was confirmed by 377 Stretch sequencer (Applied Biosystems Inc., Foster City, Calif.). To facilitate purification of recombinant SPICE (rSPICE) and VCP (rVCP) proteins, two constructs for each protein were designed. One construct encoded for six histidines at the carboxy-terminus (his tag or his), while the other encoded for a carboxy-terminus mouse IgG2a Fc domain (Fc). SPICE was substituted for VCP in three plasmids (pRelVCP1234, pApHygVCPFc, and pVCPFc; Rosengard et al. (1999) *Mol. Immunol.* 36:685–697)) previously used to express VCPFc in 293T cells. Recombinant baculoviruses were created by subcloning SPICEFc and VCPFc EcoRI/XbaI fragments into pFastBac™HTa (Bac-to-Bac® system, LTI) to create pFastBacHTaSPICEFc and pFastBacHT-aVCPFc and novel recombinant baculovirus strains containing SPICEFc and VCPFc.

TABLE 1

| Location | | Amino Acid Sequence | |
|---|---|---|---|
| SCR1: | | | |
| | SPICE | CCTIPSRPINMKFKNSVETDANANYNIGDTIEYLCLPGYRKQKMGPIYAKCTGTGWTLFNQCIKRR | (SEQ ID NO:1) |
| | VCP | CCTIPSRPINMKFKNSVETDANANYNIGDTIEYLCLPGYRKQKMGPIYAKCTGTGWTLFNQCIKRR | (SEQ ID NO:2) |
| SCR2: | | | |
| | SPICE | CPSPRDIDNGHLDIGGVDFGSSITYSCNSGYYLIGEYKSYCKLGSTGSMVWNPKAPICESVK | (SEQ ID NO:3) |
| | VCP | CPSPRDIDNGQLDIGGVDFGSSITYSCNSGYHLIGESKSYCELGSTGSMVWNPEAPICESVK | (SEQ ID NO:4) |

TABLE 1-continued

| Location | Amino Acid Sequence | |
|---|---|---|
| SCR3: | | |
| SPICE | CQLPPSISNGRHNGYNDFYTDGSWTYSCNSGYSLIGNSGVLCSGGEWSNPPTCQIVK | (SEQ ID NO:5) |
| VCP | CQSPPSISNGRHNGYEDFYTDGSWTYSCNSGYSLIGNSGVLCSGGEWSDPPTCQIVK | (SEQ ID NO:6) |
| SCR4: | | |
| SPICE | CPHPTILNGYLSSGFKRSYSYNDNVDFTCKYGYKLSGSSSSTCSPGNTWQPELPKCVR | (SEQ ID NO:7) |
| VCP | CPHPTISNGYLSSGFKRSYSYNDNVDFKCKYGYKLSGSSSSTCSPGNTWKPELPKCVR | (SEQ ID NO:8) |

Underlined residues indicate amino acid substitutions.

A baculovirus construct containing a placental alkaline phosphatase leader sequence (Mroczkowski et al (1994) *J. Biol. Chem.* 269:13522–13528) and six histidines at the carboxy-terminus was created using a PCR-based approach. Oligonucleotides 99AMR1 (5'-GCACCCGGGAGTTCTATCATGCTG TACTATTCCG-3'; SEQ ID NO:9) and HISSTOP (5'-GCTCTAGACT CGAGCTAGTGGTGGTGGTGGTGGTGGCGTA CACATTTTGGAAGTTC-3'; SEQ ID NO:10) were used. The novel SPICE and VCP PspAI/XhoI fragments were ligated into pBluescript® II KS phagemid (Stratagene, La Jolla, Calif.) and subsequently subcloned into pFastBac™ at XbaI/XhoI sites to generate pFBSPICEhis and pFBVCPhis. Concurrently, the alkaline phosphatase leader from pPbac (Stratagene) was cleaved using NheI/PspAI and ligated to generate pFBapSPICEhis and pFBapVCPhis, which were used to generate baculovirus containing SPICEhis and VCPhis.

Recombinant proteins were produced either in 293T cells (Rosengard et al. (1999) *Mol. Immunol.* 36:685–697) or in *Spodoptera frugiperda* (Sf9 cells; LTI) and affinity purified from culture supernatant using CL-4B protein A beads (Amersham Pharmacia, Uppsala, Sweden) or Ni-NTA Superflow (Qiagen, Valencia, Calif.). Recombinant proteins were dialyzed against phosphate buffered saline (PBS; LTI). Characterization of SPICEhis and VCPhis by mass spectrometry was performed (M-Scan, West Chester, Pa.).

EXAMPLE 2

Anti-VCP and Anti-SPICE Monoclonal Antibodies

Generation of anti-SPICE/VCP monoclonal antibodies (mAb). Production to anti-SPICE/VCP mAbs was performed using standard methods. Briefly, 4–6 week old Balb/c mice (Jackson, Bar Harbor, Me.) were immunized intraperitoneally with ~35 μg of recombinant VCP (rVCP, either VCPFc or VCPhis) in complete Freund's adjuvant (FA) and later boosted with ~35 μg of protein in incomplete FA. Splenic cells ($1 \times 10^8$) were fused with myeloma cells ($1 \times 10^8$; SP2/0-Ag 14 cells; ATCC #CRL 1581, Manassas, Va.). Master clones were twice subcloned and subsequently injected intraperitoneally into pristane-treated Balb/c mice. MAbs were purified from ascites fluid using Protein G Sepharose slurry (Amersham Pharmacia, Uppsala, Sweden).

Identification of wild-type VCP using polyclonal anti-SPICE/VCP antibodies. Anti-VCP mAb identified wild-type VCP in serum-free media (DMEM; Life Technologies, Inc., Rockville, Md.) from four 75 cm² flasks of BS-C-1 cells (CCL-26, ATCC) previously infected with 10 plaque-forming units/cell of vaccinia virus strain Western Reserve (WR). Medium was concentrated 1000-fold, fractionated by SDS-PAGE, and transferred to nitrocellulose membrane. Western blot analysis was performed using polyclonal anti-VCP antiserum (1:1000 dilution), followed by biotin-conjugated goat anti-mouse IgG (1:100,000 dilution; Sigma, St. Louis, Mo.), avidin-peroxidase (1:10,000), and TMB Membrane Peroxidase Substrate System Kit (Kirkegaard and Perry Laboratories, Inc. (KPL), Gaithersburg, Md.).

Mapping of anti-SPICE/VCP mAb to short consensus repeats of VCP. Nine mAb were generated from mice injected with rVCP. The binding site on VCP of each mAb was determined by flow cytometry using previously described mouse fibroblast cell lines (L-M(TK), CCL1.3; ATCC) that express 2, 3, or 4 contiguous VCP short consensus repeats (SCRs) as cell surface receptors (Rosengard et al. (1999) *Mol. Immunol.* 36:685–697). Essentially, the cells stably express SCR1–2, 2–3, 3–4, 1–3, 2–4, or 1–4 of VCP. These fibroblasts and wild-type L-cells were incubated with each mAb, followed by fluorescein-conjugated F(ab')2 goat anti-mouse IgG (50 μL; Jackson Immunoresearch, West Grove, Pa.) and analyzed on a flow cytometer (FACScan; Becton-Dickinson, San Jose, Calif.). Isotype-matched non-specific antibodies were used as negative controls. The results of these binding studies are shown in Table 2.

TABLE 2

| | | Binding to L-cells Expressing VCP-Deletion Mutants or WT L-cells | | | | | | |
|---|---|---|---|---|---|---|---|---|
| mAb | Epitope | SCR1-2 | SCR2-3 | SCR3-4 | SCR1-3 | SCR2-4 | SCR1-4 | WT |
| 5A10 | SCR1 | +++ | 0 | 0 | +++ | 0 | +++ | 0 |
| 6E5 | SCR1 | +++ | 0 | 0 | +++ | 0 | +++ | 0 |
| 3D9 | SCR2 | +++ | +++ | 0 | +++ | +++ | +++ | 0 |
| 6C4 | SCR2 | +++ | +++ | 0 | +++ | +++ | +++ | 0 |
| 2F10 | SCR3 | 0 | +++ | +++ | +++ | +++ | +++ | 0 |

TABLE 2-continued

| | | Binding to L-cells Expressing VCP-Deletion Mutants or WT L-cells | | | | | | |
|---|---|---|---|---|---|---|---|---|
| mAb | Epitope | SCR1-2 | SCR2-3 | SCR3-4 | SCR1-3 | SCR2-4 | SCR1-4 | WT |
| 5E7 | SCR3 | 0 | +++ | +++ | +++ | +++ | +++ | 0 |
| 1G1 | SCR4 | 0 | 0 | +++ | 0 | +++ | +++ | 0 |
| 5A1 | SCR4 | 0 | 0 | +++ | 0 | +++ | +++ | 0 |
| 5E1 | SCR4 | 0 | 0 | +++ | 0 | +++ | +++ | 0 |
| MOPC21 | n/a | 0 | 0 | 0 | 0 | 0 | 0 | 0 |

Detection of SPICE by mAbs using competitive ELISA. All nine mAbs detected rVCP by enzyme-linked immunosorbent assay (ELISA) (Table 3). To determine the minimum antibody concentration necessary for competitive ELISAs, each mAb was first diluted from 10 to 0.015 µg/mL and tested against VCPhis in an indirect ELISA using biotin-SP-conjugated goat anti-mouse IgG (1:5000; Jackson Immunoresearch), avidin-peroxidase (1:400; Sigma) and the Protein Detector ELISA Kit (KPL). Thereafter, 50 µL of 3 µg/mL of VCPhis was coated on a microtiter plate. Concurrently, each mAb (0.3 g/mL) was incubated for 30 min with varying amounts of SPICEhis such that the SPICEhis:mAb molar ratios were either 1:1, 2:1, 3:1, 4:1, 5:1, 10:1, or 20:1. The microtiter plates containing VCPhis were then incubated with 50 µL of the SPICEhis/mAb solutions for 1 hour, followed by the secondary antibody described above. Loss of VCPhis-binding represented competitive binding by SPICEhis. The results of this analysis are shown in Table 3.

TABLE 3

| mAb | VCP-binding | SPICE-binding |
|---|---|---|
| 5A10 | +++ | +++ |
| 6E5 | +++ | 0 |
| 3D9 | +++ | 0 |
| 6C4 | +++ | 0 |
| 2F10 | +++ | 0 |
| 5E7 | +++ | +++ |
| 1G1 | +++ | +++ |
| 5A1 | +++ | 0 |
| 5E1 | +++ | 0 |
| MOPC21 | 0 | 0 |

EXAMPLE 3

C3b and C4b Degradation

C3b or C4b degradation in the presence of SPICE and factor I. Cofactor activity was measured by incubating C3b or C4b with each cofactor at 37° C. Samples were removed at 0, 4, and 24 hours as indicated. Nine µg of C3b and C4b (Advanced Research Technologies (ART), San Diego, Calif.) were incubated with 3 µg of factor I (ART), and 6 µg of VCPhis, SPICEhis, factor H (ART) or soluble CR1 (sCR1; generously provided by Novartis Pharmaceutical, Hanover, N.J.) in a total volume of 33 µL at 37° C. as previously described (Sahu, et al. (1998) *J. Immunol.* 160:5596–5604). Ten µL were removed at 0, 4, and 24 hours, mixed with sample buffer containing 2-mercaptoethanol (2-ME; BioRad, Hercules, Calif.), boiled 2 minutes, and separated by electrophoresis on a 9% SDS-PAGE. C3b and C4b cleavage products were visualized by staining the gel with Coomassie blue.

Rate of cofactor activity of SPICEhis, VCPhis and sCR1. Kinetic experiments were performed to compare the rate of cofactor activity at limiting concentrations of recombinant factors. C3b and C4b were incubated with factor I (13 µM) and 0.65 pM of SPICEhis, VCPhis, or sCR1 in a total volume of 66 µL at 37° C. Ten µL samples were removed at time intervals indicated and subjected to electrophoresis. Coomassie-stained gels were scanned for densitometric analysis using transmissive spectrophotometer (Model 355A, Molecular Dynamics, Sunnyvale, Calif.) and analyzed using the ImageQuant 3.2 Software (Molecular Dynamics). Reported values represent OD relative to the original sample of the C3bα' or C4bα' chains. Experiments were performed 5 times with reproducible results obtained in all cases.

EXAMPLE 4

Inhibition of SPICE or VCP Cofactor Activity Using Anti-SPICE/VCP mAbs

The effect of SPICE/VCP mAb on cofactor activity was also examined. SPICE and VCP were pre-incubated with 0.5–3.0 molar equivalents of each mAb prior to the addition of C3b or C4b and factor I. SPICEhis reactions were stopped at 20 and 50 minutes for C3b and C4b, respectively. VCPhis reactions were stopped at 60 and 150 minutes for C3b and C4b, respectively. Degradation products were subjected to electrophoresis, visualized using Coomassie blue and analyzed using a densitometer. Values represent optical density (OD) relative to an equivalent sample of C34b and C4b incubated in the absence of cofactors.

EXAMPLE 5

Species Preferences of SPICE

Complement-mediated hemolysis was evaluated by determining the highest dilution of human, dog, guinea pig, and baboon (data not shown) sera that resulted in 100% hemolysis of antibody-sensitized sheep erythrocytes (EA) or unsensitized rabbit erythrocytes (Er; $1 \times 10^8$/mL GVB$^{++}$; ART), respectively (Kitamura, H. Interspecies incompatibilities of complement factors and regulators, 564, Springer-Verlag, Berlin, 1998) at 37° C. Thereafter, the sera was serially diluted in U-bottom polypropylene 96-well plates (Corning, Inc., Corning, N.Y.) until no hemolysis was detected. Reactions were stopped after 1 hour with PBS (180 µL/well). Maximum hemolysis was obtained by the addition of water instead of PBS. Plates were centrifuged and 100 µL of supernatant was read at 405 nm. Serum heated to 56° C. for 30 minutes established background hemolysis.

To determine the influence of various CRPs on complement-mediated hemolysis of EA or Er, 25 µL of serially-diluted serum was added, followed by 25 µL of 0.1–0.25 mg/mL CRP or PBS, and 50 µL of erythrocytes ($1 \times 10^8$/mL hemolysis for CRP-treated wells relative to PBS-treated wells at identical serum dilutions. All experiments were performed between 3 and 10 times, and reproducible results were obtained in all cases.

EXAMPLE 6

Detection and Differentiation of Orthopoxviruses Vaccinia Virus in Serum/Plasma Using Restriction Fragment Length Polymorphism Analysis Extraction of Viral DNA from Serum. Using heparin for anticoagulation, mice were bled from the eye and the blood was separated into plasma and blood cells by centrifugation. Water was added to the plasma to make a total volume of 200 µL. Using the High Pure Viral Nucleic Acid Kit (Roche), 200 µL of working solution (binding buffer:polyA carrier RNA at 50:1 (v/v)) was added to each plasma sample. Subsequently, 50 µL of Proteinase K was added to each sample, mixed, and incubated for 10 minutes at 72° C. After the incubation, samples were mixed with 100 µL isopropanol. Samples were pipetted into the upper reservoir of the High Pure filter tube/collection tube assembly. Samples were centrifuged for 1 minute at 10,000 rpm in a standard table top centrifuge. The flow-through was discarded, 500 µL of inhibitor removal buffer was added to the upper reservoir, and the sample was centrifuged for 1 minute at 10,000 rpm. Wash buffer was next added (450 µL) and the sample was centrifuged. Water was added to the sample and allowed to incubate for 10 minutes at room temperature followed by a final centrifugation at 10,000 rpm to elute the DNA.

Amplification of VCP/SPICE gene sequence. Using primer pairs flanking the terminal regions of the VCP and SPICE genes (Sense Primer: 5'Bgl SCR1-GAAGATCTTTGTACTATTCCGTCACGACCCATTAAT; SEQ ID NO:11 and Antisense Primer: 3' Nhe1 SCR4-CTAGCTAGCGCGTACACATTTTGGAAGT-TCCGGCTT; SEQ ID NO:12) a standard PCR reaction was performed on serum-purified viral DNA. Thirty µL of purified DNA was added to 34 µL of water and 36 µL of master mix (8 µL Sense Primer, 8 µL Antisense Primer, 4 µL MgCl$_2$ (Roche), 10 µL 10×PCR Buffer, 2 µL dNTPs, 0.5 µL Taq Polymerase (Invitrogen), and 3.5 µL water). DNA was amplified for 50 cycles (1 minute at 95° C., 1 minute at 65° C., 1 minute at 720C), extended for 5 minutes at 72° C., and stored at 4° C.

Restriction digestion of amplified products. Endonuclease digestion with SspI was performed using standard methods. DNA fragments were resolved by gel electrophoresis using a 1.5% agarose gel in TAE buffer.

To test the sensitivity of the PCR step, various volumes (0.001 µL-4 µL) of vaccinia virus (1×10$^8$ pfu/mL) were added to 80 µL of serum/plasma and the VCP fragment was amplified as described herein. Resolution by gel electrophoresis showed a single VCP fragment was amplified from all volumes tested.

What is claimed is:

1. An isolated monoclonal antibody which specifically binds SPICE and VCP.

2. A composition comprising least one isolated monoclonal antibody which specifically binds SPICE and VCP and a pharmaceutically acceptable carrier.

3. A method of modulating side effects of vaccinia virus vaccination comprising administering the composition of claim 2.

4. A method of diagnosing the presence of variola virus or vaccinia virus infection comprising detecting SPICE or VCP in a sample comprising the steps of:

(a) contacting an antibody of claim 1 with a sample so that said antibody binds an epitope of SPICE or VCP if the epitope is contained in sample;

(b) washing the sample; and (c) detecting bound antibody, wherein detecting bound antibody indicates the presence of infection.

5. The method of claim 4 wherein detecting SPICE or VCP comprises the use of an enzyme-linked immunoassay.

6. A kit for detecting the presence of SPICE or VCP polypeptides comprising the antibody of claim 1.

* * * * *

UNITED STATES PATENT AND TRADEMARK OFFICE
CERTIFICATE OF CORRECTION

PATENT NO. : 6,783,759 B2
APPLICATION NO. : 10/108311
DATED : August 31, 2004
INVENTOR(S) : Ariella M. Rosengard It is certified that error appears in the above-identified patent and that said Letters Patent is hereby corrected as shown below:

At column 17, line 24: Please delete "0.3g/mL" and insert --0.3 ìg/mL--.

At column 18, line 67: Please insert --in GVB++). Reported values represent percent of maximum-following "(1 X $10^8$ mL)".

At column 20, line 15: Please delete "720C" and insert --72°C--.

At column 25, line 23: Please insert --at-- between the words "comprising" and "least".

Signed and Sealed this

Thirtieth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 6,783,759 B2  Page 1 of 1
APPLICATION NO. : 10/108311
DATED : August 31, 2004
INVENTOR(S) : Ariella M. Rosengard It is certified that error appears in the above-identified patent and that said Letters Patent is hereby corrected as shown below:

At column 17, line 24: Please delete "0.3g/mL" and insert --0.3 µg/mL--.

At column 18, line 67: Please insert --in GVB++). Reported values represent percent of maximum-following "(1 X $10^8$ mL)"--.

At column 20, line 15: Please delete "720C" and insert --72°C--.

At column 25, line 23: Please insert --at-- between the words "comprising" and "least".

This certificate supersedes the Certificate of Correction issued September 30, 2008.

Signed and Sealed this

Eighteenth Day of November, 2008

JON W. DUDAS
*Director of the United States Patent and Trademark Office*

SEQUENCE LISTING

<160> NUMBER OF SEQ ID NOS: 12

<210> SEQ ID NO 1
<211> LENGTH: 66
<212> TYPE: PRT
<213> ORGANISM: Variola virus

<400> SEQUENCE: 1

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg
65

<210> SEQ ID NO 2
<211> LENGTH: 66
<212> TYPE: PRT
<213> ORGANISM: Vaccinia virus

<400> SEQUENCE: 2

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr

```
                35                  40                  45
Ala Lys Cys Thr Gly Thr Gly Trp Thr Leu Phe Asn Gln Cys Ile Lys
    50                  55                  60

Arg Arg
65

<210> SEQ ID NO 3
<211> LENGTH: 62
<212> TYPE: PRT
<213> ORGANISM: Variola virus

<400> SEQUENCE: 3

Cys Pro Ser Pro Arg Asp Ile Asp Asn Gly His Leu Asp Ile Gly Gly
1               5                  10                  15

Val Asp Phe Gly Ser Ser Ile Thr Tyr Ser Cys Asn Ser Gly Tyr Tyr
            20                  25                  30

Leu Ile Gly Glu Tyr Lys Ser Tyr Cys Lys Leu Gly Ser Thr Gly Ser
        35                  40                  45

Met Val Trp Asn Pro Lys Ala Pro Ile Cys Glu Ser Val Lys
    50                  55                  60

<210> SEQ ID NO 4
<211> LENGTH: 62
<212> TYPE: PRT
<213> ORGANISM: Vaccinia virus

<400> SEQUENCE: 4

Cys Pro Ser Pro Arg Asp Ile Asp Asn Gly Gln Leu Asp Ile Gly Gly
1               5                  10                  15

Val Asp Phe Gly Ser Ser Ile Thr Tyr Ser Cys Asn Ser Gly Tyr His
            20                  25                  30

Leu Ile Gly Glu Ser Lys Ser Tyr Cys Glu Leu Gly Ser Thr Gly Ser
        35                  40                  45

Met Val Trp Asn Pro Glu Ala Pro Ile Cys Glu Ser Val Lys
    50                  55                  60

<210> SEQ ID NO 5
<211> LENGTH: 57
<212> TYPE: PRT
<213> ORGANISM: Variola virus

<400> SEQUENCE: 5

Cys Gln Leu Pro Pro Ser Ile Ser Asn Gly Arg His Asn Gly Tyr Asn
1               5                  10                  15

Asp Phe Tyr Thr Asp Gly Ser Trp Thr Tyr Ser Cys Asn Ser Gly Tyr
            20                  25                  30

Ser Leu Ile Gly Asn Ser Gly Val Leu Cys Ser Gly Gly Glu Trp Ser
        35                  40                  45

Asn Pro Pro Thr Cys Gln Ile Val Lys
    50                  55

<210> SEQ ID NO 6
<211> LENGTH: 57
<212> TYPE: PRT
<213> ORGANISM: Vaccinia virus

<400> SEQUENCE: 6

Cys Gln Ser Pro Pro Ser Ile Ser Asn Gly Arg His Asn Gly Tyr Glu
1               5                  10                  15
```

Asp Phe Tyr Thr Asp Gly Ser Trp Thr Tyr Ser Cys Asn Ser Gly Tyr
            20                  25                  30

Ser Leu Ile Gly Asn Ser Gly Val Leu Cys Ser Gly Gly Glu Trp Ser
            35                  40                  45

Asp Pro Pro Thr Cys Gln Ile Val Lys
        50                  55

<210> SEQ ID NO 7
<211> LENGTH: 58
<212> TYPE: PRT
<213> ORGANISM: Variola virus

<400> SEQUENCE: 7

Cys Pro His Pro Thr Ile Leu Asn Gly Tyr Leu Ser Ser Gly Phe Lys
1               5                   10                  15

Arg Ser Tyr Ser Tyr Asn Asp Asn Val Asp Phe Thr Cys Lys Tyr Gly
            20                  25                  30

Tyr Lys Leu Ser Gly Ser Ser Ser Thr Cys Ser Pro Gly Asn Thr
            35                  40                  45

Trp Gln Pro Glu Leu Pro Lys Cys Val Arg
        50                  55

<210> SEQ ID NO 8
<211> LENGTH: 58
<212> TYPE: PRT
<213> ORGANISM: Vaccinia virus

<400> SEQUENCE: 8

Cys Pro His Pro Thr Ile Ser Asn Gly Tyr Leu Ser Ser Gly Phe Lys
1               5                   10                  15

Arg Ser Tyr Ser Tyr Asn Asp Asn Val Asp Phe Lys Cys Lys Tyr Gly
            20                  25                  30

Tyr Lys Leu Ser Gly Ser Ser Ser Thr Cys Ser Pro Gly Asn Thr
            35                  40                  45

Trp Lys Pro Glu Leu Pro Lys Cys Val Arg
        50                  55

<210> SEQ ID NO 9
<211> LENGTH: 33
<212> TYPE: DNA
<213> ORGANISM: Artificial Sequence
<220> FEATURE:
<223> OTHER INFORMATION: Synthetic Oligonucleotide.

<400> SEQUENCE: 9
gcacccggga gttctatcat gctgtactat tcc                                33

<210> SEQ ID NO 10
<211> LENGTH: 56
<212> TYPE: DNA
<213> ORGANISM: Artificial Sequence
<220> FEATURE:
<223> OTHER INFORMATION: Synthetic Oligonucleotide.

<400> SEQUENCE: 10
gctctagact cgagctagtg gtggtggtgg tggtggcgta cacatttgg aagttc        56

<210> SEQ ID NO 11
<211> LENGTH: 36
<212> TYPE: DNA
<213> ORGANISM: Artificial Sequence
<220> FEATURE:

-continued

```
<223> OTHER INFORMATION: Synthetic Oligonucleotide.

<400> SEQUENCE: 11
gaagatcttt gtactattcc gtcacgaccc attaat                    36

<210> SEQ ID NO 12
<211> LENGTH: 36
<212> TYPE: DNA
<213> ORGANISM: Artificial Sequence
<220> FEATURE:
<223> OTHER INFORMATION: Synthetic Oligonucleotide.

<400> SEQUENCE: 12
ctagctagcg cgtacacatt ttggaagttc cggctt                    36
```